(12) United States Patent
Wilson

(10) Patent No.: US 6,293,995 B2
(45) Date of Patent: *Sep. 25, 2001

(54) CHROMATOGRAPH HAVING A GAS STORAGE SYSTEM

(75) Inventor: William H. Wilson, Newark, DE (US)

(73) Assignee: Agilent Technologies, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/531,378

(22) Filed: Mar. 21, 2000

Related U.S. Application Data

(62) Division of application No. 09/126,530, filed on Jul. 30, 1998, now Pat. No. 6,063,166.

(51) Int. Cl.[7] .................. B01D 15/08; B01D 53/04; B01D 53/22
(52) U.S. Cl. .................. 95/23; 95/56; 95/82; 95/127
(58) Field of Search .................. 95/55, 56, 82–89, 95/127, 23; 96/4–14, 101–108, 130, 143

(56) References Cited

U.S. PATENT DOCUMENTS

| Re. 35,725 | * | 2/1998 | Briesacher et al. ............. 96/108 X |
| 3,357,157 | * | 12/1967 | O'Donnell ..................... 95/84 |
| 3,400,514 | * | 9/1968 | Noda ........................... 96/106 X |
| 3,455,817 | * | 7/1969 | Modell .......................... 95/82 X |
| 3,589,171 | * | 6/1971 | Haley ........................... 95/56 X |
| 3,624,986 | * | 12/1971 | Shoemake ....................... 96/102 X |
| 3,638,396 | * | 2/1972 | Lovelock ........................ 95/56 |
| 3,638,397 | * | 2/1972 | Charlton ........................ 95/56 |
| 3,712,028 | * | 1/1973 | Deans ........................... 95/82 |
| 3,818,679 | * | 6/1974 | Klass et al. .................... 95/280 |
| 3,971,768 | * | 7/1976 | Peters et al. ................... 526/68 |
| 4,230,464 | * | 10/1980 | Bonmati et al. ................. 95/22 |
| 4,238,204 | * | 12/1980 | Perry ........................... 95/56 X |
| 4,472,176 | * | 9/1984 | Rubin ........................... 95/56 |
| 4,537,759 | * | 8/1985 | Walker et al. ................... 95/82 X |
| 4,762,535 | * | 8/1988 | Pez et al. ...................... 95/44 |
| 4,994,096 | * | 2/1991 | Klein et al. .................... 95/82 X |
| 5,108,466 | * | 4/1992 | Klein et al. .................... 95/82 X |
| 5,205,841 | * | 4/1993 | Vaiman .......................... 95/56 X |
| 5,205,843 | * | 4/1993 | Kaschemekat et al. ............. 95/39 |
| 5,431,712 | * | 7/1995 | Henderson et al. ............... 95/23 X |
| 5,545,252 | * | 8/1996 | Hinshaw et al. ................. 95/23 X |
| 5,567,227 | * | 10/1996 | Henderson ....................... 95/82 X |
| 5,622,682 | * | 4/1997 | Tom ............................. 423/230 |
| 5,698,011 | * | 12/1997 | Chung et al. .................... 95/45 |
| 5,895,519 | * | 4/1999 | Lorimer ......................... 96/108 X |
| 6,063,166 | * | 5/2000 | Wilson .......................... 96/4 |

* cited by examiner

Primary Examiner—Robert H. Spitzer

(57) ABSTRACT

A chromatograph includes an inlet for receiving a sample and a pressurized hydrogen gas flow and in response providing a sample/fluid mixture; a separation column located in a temperature-controlled zone for receiving the sample/fluid mixture and for providing a column effluent stream; a detector for receiving the effluent stream and for providing a detector output stream; and a gas storage system for receiving the detector output stream (and optionally a split flow and a septum purge flow in the instance of a split/splitless inlet) and for storing the received gas stream for subsequent reuse. In the preferred embodiments of the gas storage system, a plurality of metal hydride storage (MHS) systems are used.

6 Claims, 5 Drawing Sheets

CHROMATOGRAPH HAVING A GAS STORAGE SYSTEM

CROSS REFERENCE TO RELATED APPLICATION

This application is a division of application Ser. No. 09/126,530 filed on even date herewith, in the name of William H. Wilson, and entitled "CHROMATOGRAPH HAVING A GAS STORAGE SYSTEM", now U.S. Pat. No. 6,063,166, filed Jul. 30, 1998.

FIELD OF THE INVENTION

The present invention relates to methods and apparatus for use in analytical instrumentation for the detection of an analyte in a carrier fluid, and in particular to analytical instrumentation having a closed-loop system for storage and reuse of hydrogen carrier gas.

BACKGROUND OF THE INVENTION

A simplified schematic view of a conventional chromatograph 100 is shown in FIG. 1. The illustrated chromatograph 100 is representative of a Hewlett-Packard 6890 Gas Chromatograph. Analytical instruments such as the gas chromatograph 100 are known for use in determining the chemical composition of a sample which is typically injected at an inlet 112 into a carrier gas stream provided by a carrier gas source 111 through a manifold 113. A fluid mixture of the sample and the carrier gas is directed through a separation column 114 located within an oven 116 and exposed to a controlled temperature environment provided by a heater 118. The separation column 114 includes a stationary phase coating on the interior of the column. The interaction of the constituent compounds in the sample with the stationary phase cause differing chemical compounds in the sample to travel through the separation column at different rates and to leave the separation column at different times. The presence of compounds in the column effluent gas is sensed by a detector 124. A detector output signal is provided to a controller 126 and a computer 122 on signal lines 128,130. The compound of interest is typically called an analyte.

A significant shortcoming in the conventional gas chromatograph is due to the loss of one or more gas streams that are typically vented to the atmosphere from the inlet 112 or the detector 124. The majority of the composition of such streams is carrier gas; for example, if the inlet 112 is constructed as a split/splitless inlet, much of the carrier gas employed by the chromatograph 100 is vented away from the inlet 112. Accordingly, a column with a 1 ml/min flow rate and a split ratio of 100:1 will vent 100 times the amount of gas actually required to carry a sample through the column 114 for an analysis. Six liters of carrier gas at inlet pressure are typically lost to the surrounding environment during one hour of analysis. However, if the carrier gas were to be conserved, such a volume of gas could easily supply a column flow for many more hours of continuous operation.

The high rate of consumption of carrier gas observed in the conventional apparatus is one of the major factors that have inhibited the development of portable instrumentation, and has also limited the deployment of most bench top (i.e., non-portable) chromatographs in underdeveloped areas of the world where cylinders of carrier gas are in short supply.

There thus exists a need for analytical instrumentation that employs a carrier gas storage system wherein, among other factors, the flow of the carrier fluid is conserved and reused to an extent satisfactory for most analytical applications.

SUMMARY OF THE INVENTION

The advantages of the invention are achieved in a preferred embodiment of an analytical instrument, preferably provided in the form of a chromatograph, wherein a closed loop carrier gas storage system receives the gas streams that would be otherwise be vented to the atmosphere in a conventional apparatus, filters the received gas streams in order to remove the residual impurities, and stores the filtered gas stream in a gas storage system, such that the stored gas may thereafter be reused.

The preferred embodiment includes an inlet for receiving a sample and a pressurized stream of carrier gas supplied from a carrier gas reservoir, and in response, providing a sample/fluid mixture and (in some embodiments that operate a split/splitless inlet) an inlet output stream in the form of a combination of a split flow and a purge flow; a separation column located in a temperature-controlled compartment for receiving the sample/fluid mixture and for providing a column effluent stream; a detector for receiving the column effluent stream and providing in response a detector output signal and a detector output stream; and a gas storage system for filtering and storing the received gas streams for subsequent reuse. The detector generates an output signal, whereby one or more characteristics of the effluent stream that are related to the analyte of interest may be represented by the output signal.

Certain embodiments may further include a control system including a computer for sensing the volumetric flow rate of the fluid mixture entering the column and for generating a respective flow rate signal and for sensing the column input pressure and generating a respective input pressure signal, and an electronic pneumatic controller including means for receiving the flow rate signal and input pressure signal, for controlling the valve so as to control the input pressure and the volumetric flow rate of the carrier fluid.

DETAILED DESCRIPTION OF THE PREFERRED EMBODIMENT

The present invention will find useful application in a variety of analytical systems that operate with use of hydrogen gas as a carrier gas for detection of an analyte present in one or more carrier gas streams. Gases are the preferred fluids according to the practice of the present invention, and hydrogen gas is the preferred carrier gas, and therefore the following description of the invention will include a description of the arrangement, construction, and operation of a gas chromatographic analytical system (hereinafter, a chromatograph).

For the purposes of the following description, the terms "fluid" and "pneumatic" will be considered to pertain to all types of fluids. "Fluid-handling function" refers to at least one of the following functions with respect to one or more fluid streams: initiation; distribution; and redirection; termination; control of temperature, pressure or flow rate; and sensing of temperature, pressure, or flow rate. "Fluid-handling functional device" refers to a device that provides one or more fluid-handling functions with respect to one or more fluid streams. "Electronic pneumatic control" and "EPC" refers to programmed electronic control of fluids and fluid handling functions, among which are included the control of volumetric flow rate and pressure of a fluid stream in a chromatograph, as for example in accordance with the invention disclosed by U.S. Pat. No. 4,994,096, and U.S. Pat. No. 5,108,466 in the names of Klein, et al., the disclosures of which are incorporated herein by reference, and to subsequent advances known in the art for programmed electronic pneumatic control of pressure, temperature, and/or flow rate of fluids in a chromatograph.

In a significant departure from the prior art, the present invention will be understood to overcome a major problem of chromatographic systems that employ a conventional carrier gas source, and also will be understood to provide improved detection of a wide range of analytes present in a fluid stream.

In the embodiments illustrated in the Figures and described below, like nomenclature and numerical identifiers refer to identical or equivalent structures; a single line indicates an electronic signal line capable of transmitting an electronic signal; and double parallel lines indicate a pneumatic flow path capable of bearing a fluid stream.

Figure 1:
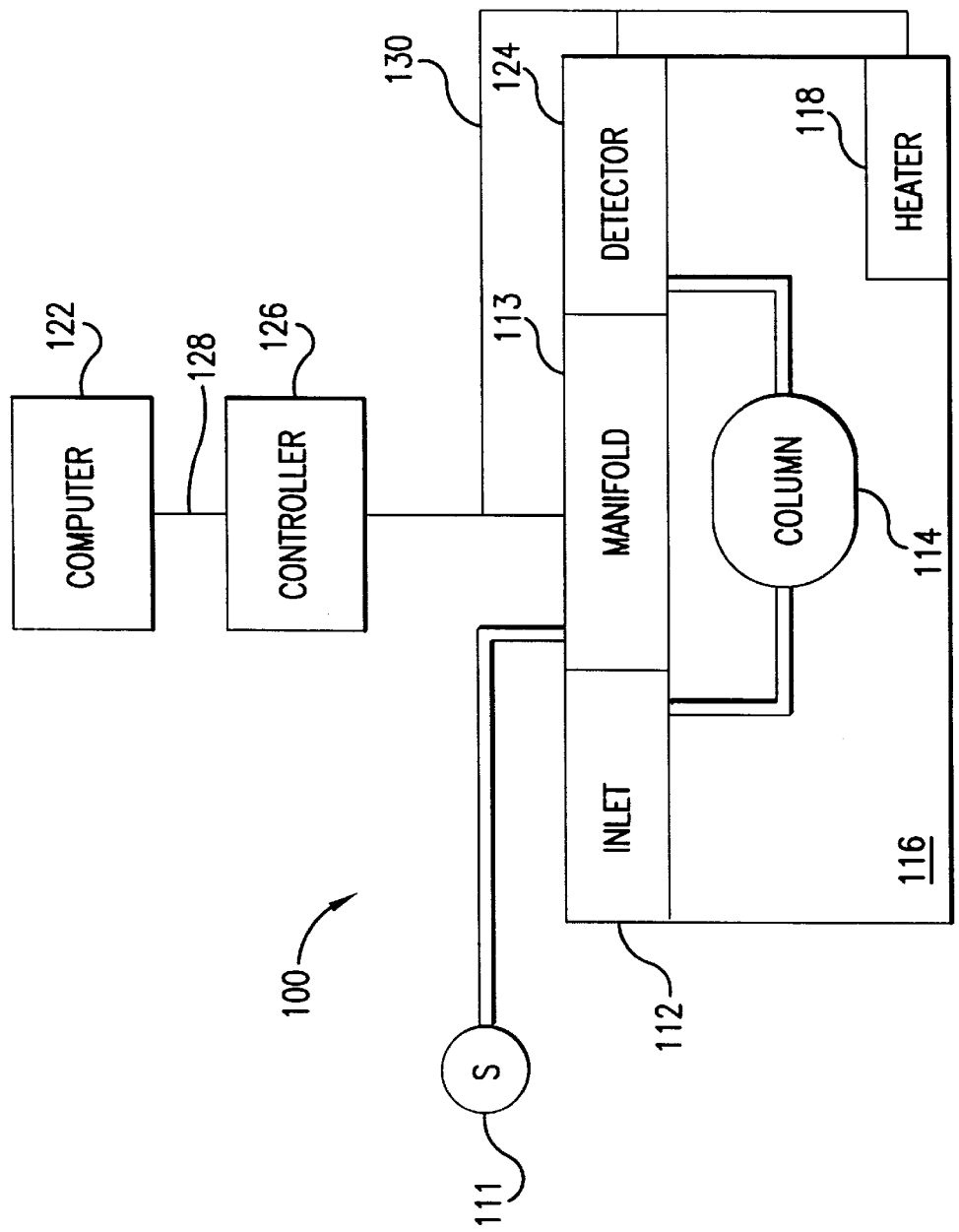
FIG. 1 is a simplified block diagram of an analytical instrument constructed as a chromatograph in accordance with the prior art.
Figure 2:
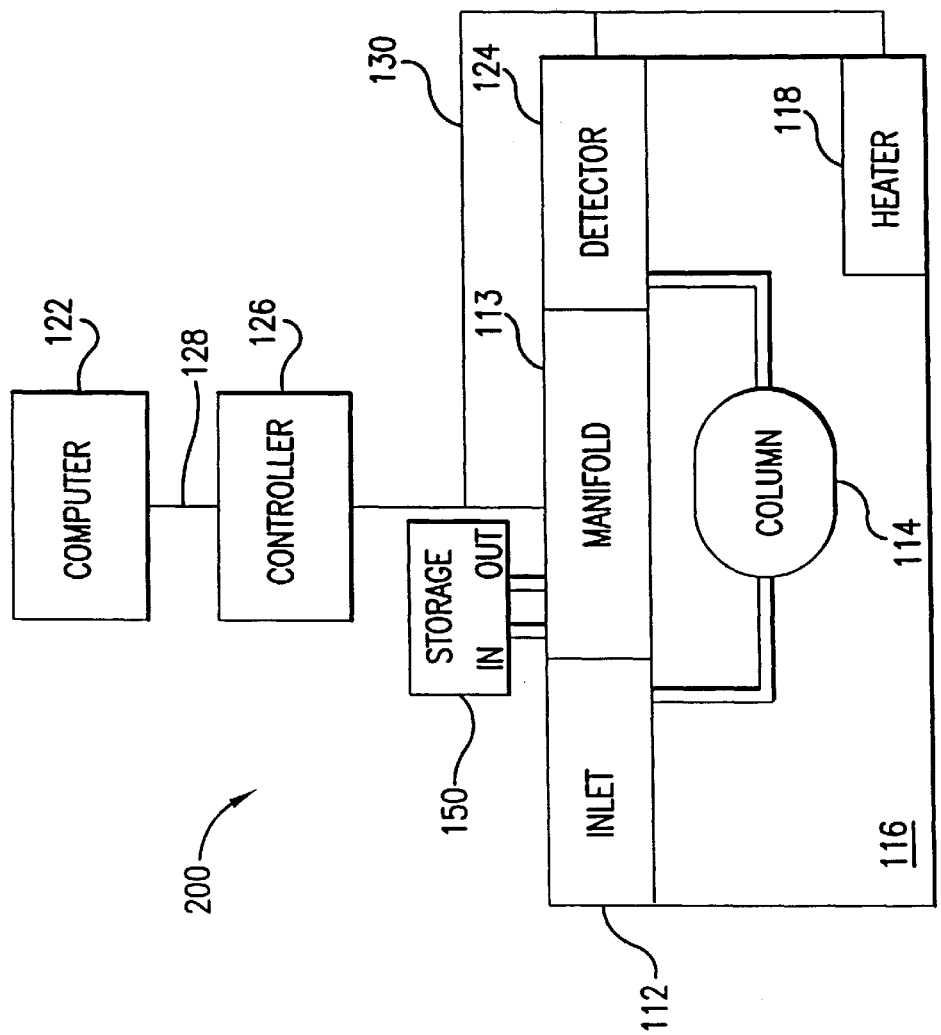
FIG. 2 is a simplified schematic view of a preferred embodiment of an analytical instrument constructed according to the present invention.

A first preferred embodiment of an analytical instrument is shown in FIG. 2 and is generally designated as a chromatograph 200. The illustrated chromatograph 200 is designed to operate using hydrogen gas as its carrier fluid. Accordingly, a hydrogen gas storage system 150 is initially charged with hydrogen gas. The manifold 113 is especially configured to include selectable pneumatic pathways for receiving the combined hydrogen gas flows that would otherwise be vented from the chromatograph 200 (such as from the detector 124 and/or the inlet 112). For example, in an embodiment wherein the inlet 112 is optionally provided in the form of a split/splitless inlet, the carrier gas flow from the storage system 150 is divided by the manifold 113 into three streams. A first stream is directed to a septum purge line, a second stream is directed to a split line, and a third stream is directed to the column 114. A chemical trap (not shown) may be employed in the manifold 113 on the split line to prevent most of the sample material from passing through the split line, such that the compounds capable of traversing the chemical trap are restricted to volatile compounds. The output of the column 114, septum purge line, and the split line may then be combined in manifold 113 and directed under the control of the controller 126 as an "incoming" gas stream to the gas storage system 150. As will now be described, the gas storage system 150 then filters the incoming gas stream and stores the hydrogen gas component of such incoming gas stream for subsequent reuse as the carrier gas needed by the chromatograph 200.

Figure 3:
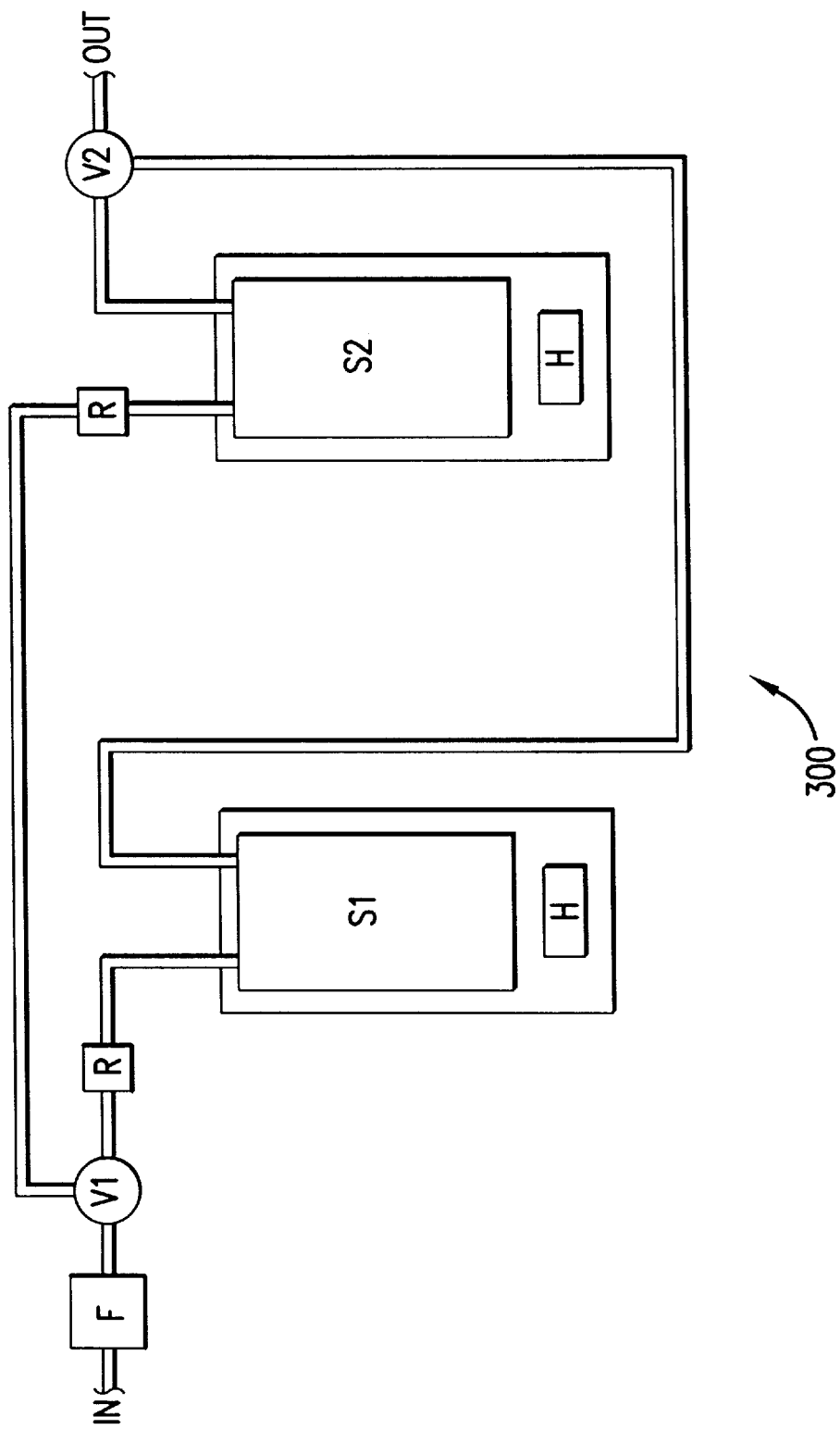
FIG. 3 is a simplified schematic view of a first preferred embodiment of a gas storage system operable in the instrument of FIG. 2.

As illustrated in FIG. 3, a first preferred embodiment of a gas storage system 300 may be constructed to include first and second valves V1, V2; flow restrictors R, a filter F, and first and second metal hydride storage (MHS) systems S1, S2 each having heaters H. The filter F may be provided in the form of a chemical filter, an absorbent trap, or a noble metal membrane that passes only hydrogen. In certain applications, the gas storage system 150 may also incorporate a pumping system constructed in the form of an electrochemical pump (not shown) operable to boost the pressure of the incoming gas flow so as to better charge the metal hydride storage systems S1, S2.

A storage cycle may be understood as follows. The system S1 is initially fully charged with hydrogen provided by an external source (not shown), and the system S2 is initially evacuated. The system S1 is heated to approximately 60 degrees Centigrade while the system S2 remains at ambient temperature. The heated environment in system S1 generates approximately 100 PSI of hydrogen pressure in system S1 and allows valve V2 to be actuated to provide hydrogen gas to the storage system output, such that the inlet 112 receives the hydrogen gas at a selectable hydrogen gas pressure. Meanwhile, an "incoming" gas stream is developed from the gas streams from the inlet 112 and/or detector 124 that would ordinarily be vented to the atmosphere. The incoming gas stream is first passed through filter F and the resulting filtered gas stream is directed to the evacuated system S2 through a restrictor R. The system S2 then begins to charge with hydrogen while the system S1 continues to be depleted due to the demands of the chromatograph 200 for hydrogen gas. When the system S1 is nearly depleted, the system S2 is heated to 60 degrees Centigrade and the valves V1, V2 are actuated to provide hydrogen gas to the system output from the system S2, and to redirect the incoming flow to the system S1. As the system S1 drops in temperature, it begins to absorb hydrogen from the incoming flow thus received, thereby storing the hydrogen for subsequent re-use. This storage cycle may be repeated so as to provide a sufficient and uninterrupted supply of carrier gas for repeated use of the chromatograph 200.

Figure 4:
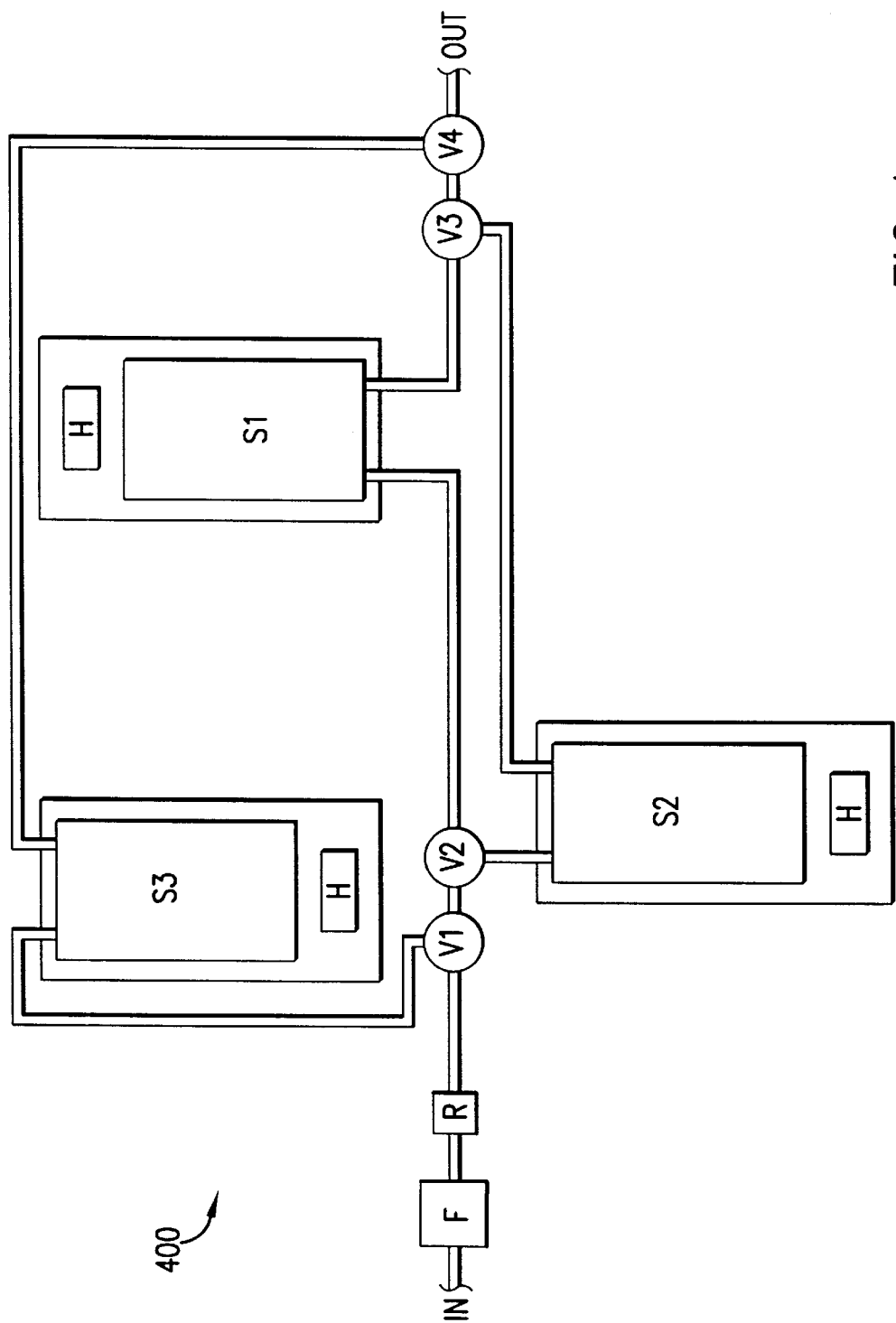
FIG. 4 is a simplified schematic view of a second preferred embodiment of a gas storage system operable in the instrument of FIG. 2.
Figure 5A:
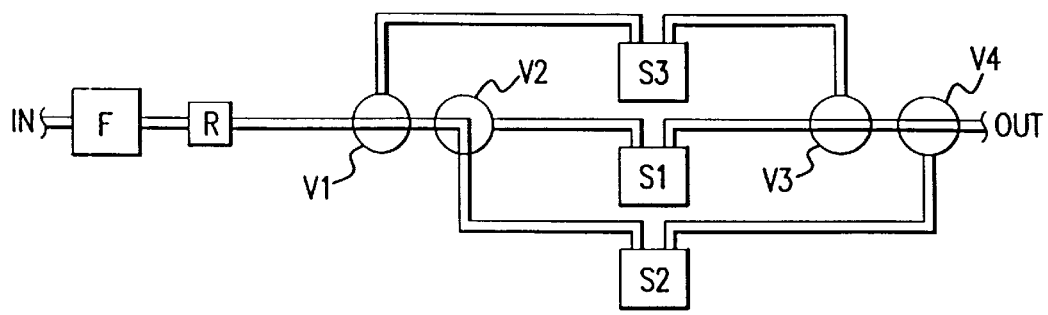
FIGS. 5A–5C are simplified schematic representations of the valve sequence operable in the second preferred embodiment of the gas storage system of FIG. 4.
Figure 5B:
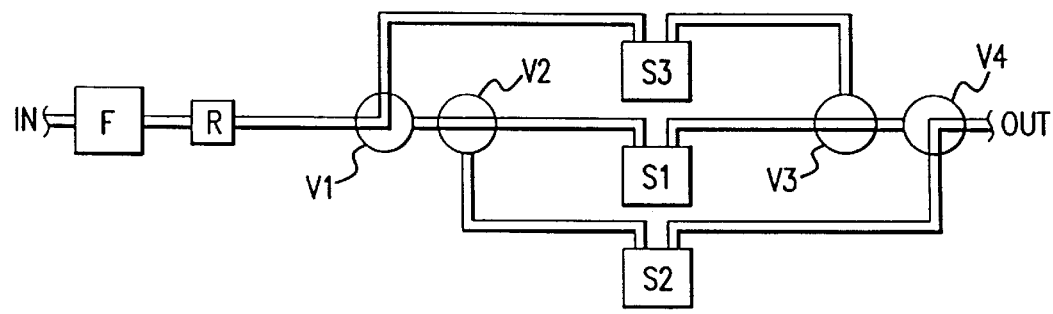
Figure 5C:
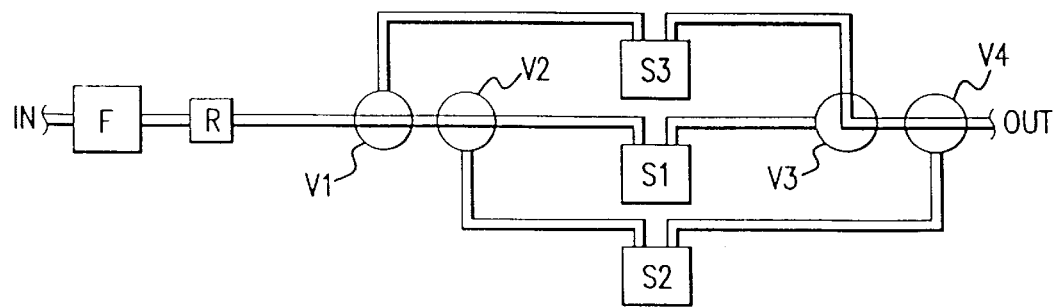

As illustrated in FIGS. 4–5, a second preferred embodiment of a gas storage system 400 may be constructed to include certain components of like nomenclature and accordingly of identical construction to those already described with reference to FIG. 3, but with the addition of a third metal hydride storage (MHS) system S3 and third and fourth valves V3, V4. As shown in FIG. 5A, the system S1 is initially charged with hydrogen and systems S2 and S3 are evacuated. Valve V1 directs the incoming flow to valve V2 so as to bypass system S3 and thereafter into the system S2. Meanwhile, system S1 is heated to generate an elevated hydrogen gas pressure therein. Valve V3 directs a hydrogen gas flow from system S1 to valve V4 which then directs the hydrogen gas flow to the storage system output. System S2 continues to collect hydrogen gas while system S3 is idle. As shown in FIG. 5B, when system S1 is sufficiently depleted of hydrogen gas, valve V1 is actuated so as to direct the incoming flow received at the storage system input to system S3. Valve V3 is actuated to isolate systems S1 and S3. Valve V4 is actuated to direct a flow of hydrogen gas from the newly charged system S2 to the storage system output. As shown in FIG. 5C, valves V1 and V2 may be actuated to direct incoming flow to the system S1. Valves V2 and V4 are actuated to isolate system S2 and valve V3 is set to allow hydrogen gas to flow from system S3 through valves V3 and V4 to the storage system output.

In the above described embodiments, the hydrogen gas is circulated in a closed loop storage system. Accordingly, the chromatograph 200 can operate for an indefinite period. For example, the only path by which hydrogen gas would be lost in chromatograph 200 would be by leaks present in the pneumatic lines, fittings, connectors, and other hydrogen bearing portions of the chromatograph 200. The propensity for such leaks may be reduced by techniques and practices known to those skilled in the art.

Storage of hydrogen gas is an advantage for the construction of: portable or hand-held chromatographs, remotely situated "online" chromatographs for environmental monitoring or process control, and bench top chromatographs for use in underdeveloped countries where a supply of conventional gas cylinders is unreliable or simply not feasible.

Although hydrogen permits the fastest chromatography, its use has heretofore been avoided because of the potential explosion hazard. Accordingly, because the carrier gas is conserved, the illustrated chromatograph 200 may be constructed for safe operation with hydrogen carrier gas. That is, the hydrogen gas may be maintained in a closed loop such that much of the hazard presented by the use of hydrogen gas is contained. This would permit the chromatograph 200 to be placed in an adverse environment without compromising most safety requirements.

Furthermore, the storage of the hydrogen gas in a closed loop system minimizes the chances for contamination of the hydrogen gas stream. The analytical performance of the illustrated chromatograph 200 is accordingly enhanced.

While the invention has been described and illustrated with reference to specific embodiments, those skilled in the art will recognize that modification and variations may be made without departing from the principles of the invention as described herein above and set forth in the following claims.

What is claimed is:

1. A method for analyzing an analyte comprising the steps of:

receiving a hydrogen gas stream and a sample containing the analyte, providing a sample/fluid mixture in response to receiving the hydrogen gas stream and the sample containing the analyte;

receiving the sample/fluid mixture;

providing a column effluent stream in response to receiving the sample/fluid mixture;

receiving the column effluent stream;

providing an output stream in response to receiving the column effluent stream;

providing a signal representative of a characteristic of the analyte;

receiving an incoming gas stream in the form of the output stream and a portion of the hydrogen gas stream not present in the sample/fluid mixture;

filtering the incoming gas stream to provide a filtered stream; and storing the filtered stream so as to retain a conserved quantity of hydrogen gas suitable for reuse as the hydrogen gas stream.

2. The chromatograph of claim 1, further comprising the steps of:

sensing a volumetric flow rate of the sample/fluid mixture; and generating a flow rate signal corresponding to the volumetric flow rate of the sample/fluid mixture.

3. The chromatograph of claim 2, further comprising the step of:

receiving the flow rate signal corresponding to the volumetric flow rate of the sample/fluid mixture; and controlling a volumetric flow rate of the hydrogen gas stream in response the flow rate signal corresponding to the volumetric flow rate of the sample/fluid mixture.

4. A method for analyzing an analyte comprising the steps of:

providing hydrogen gas and a sample containing the analyte;

producing a sample/fluid mixture from the hydrogen gas and the sample;

producing a signal representative of a characteristic of the analyte in the sample/fluid mixture; and producing a gas stream containing a portion of the hydrogen gas not present in the sample/fluid mixture.

5. The method of claim 4, further comprising the step of filtering the gas stream to form a filtered stream.

6. The method of claim 5, further comprising the step of storing the filtered stream so as to retain a conserved quantity of the hydrogen gas suitable for reuse.

* * * * *